(12) United States Patent
Xue et al.

(10) Patent No.: US 7,142,907 B2
(45) Date of Patent: Nov. 28, 2006

(54) METHOD AND APPARATUS FOR ALGORITHM FUSION OF HIGH-RESOLUTION ELECTROCARDIOGRAMS

(75) Inventors: Joel Q. Xue, Germantown, WI (US); Donald Eugene Brodnick, Cedarburg, WI (US); Paul P. Elko, River Hills, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 508 days.

(21) Appl. No.: 10/604,209

(22) Filed: Jul. 1, 2003

(65) Prior Publication Data
US 2005/0004481 A1    Jan. 6, 2005

(51) Int. Cl.
*A61B 5/0402* (2006.01)
(52) U.S. Cl. ..................................... 600/509

(58) Field of Classification Search ......... 604/509–524
See application file for complete search history.

(56) References Cited

U.S. PATENT DOCUMENTS

| | | | |
|---|---|---|---|
| 5,228,450 A * | 7/1993 | Sellers | 600/524 |
| 5,921,940 A * | 7/1999 | Verrier et al. | 600/518 |
| 6,169,919 B1 * | 1/2001 | Nearing et al. | 600/518 |
| 2003/0060724 A1 * | 3/2003 | Thiagarajan et al. | 600/515 |

* cited by examiner

*Primary Examiner*—Scott M. Getzow
(74) *Attorney, Agent, or Firm*—Ostrager Chong Flaherty & Broitman P.C.

(57) ABSTRACT

A system and a method for noninvasive ECG detection and diagnosis. The system comprises a multiplicity of electrodes applied to a patient, a data acquisition system for acquiring high-resolution ECG data from the patient; and a processor programmed to process the acquired data in accordance with two or more different ECG analysis algorithms, and then derive a prediction score for a particular clinical end point as a function of the respective results of those ECG analysis algorithms.

26 Claims, 5 Drawing Sheets

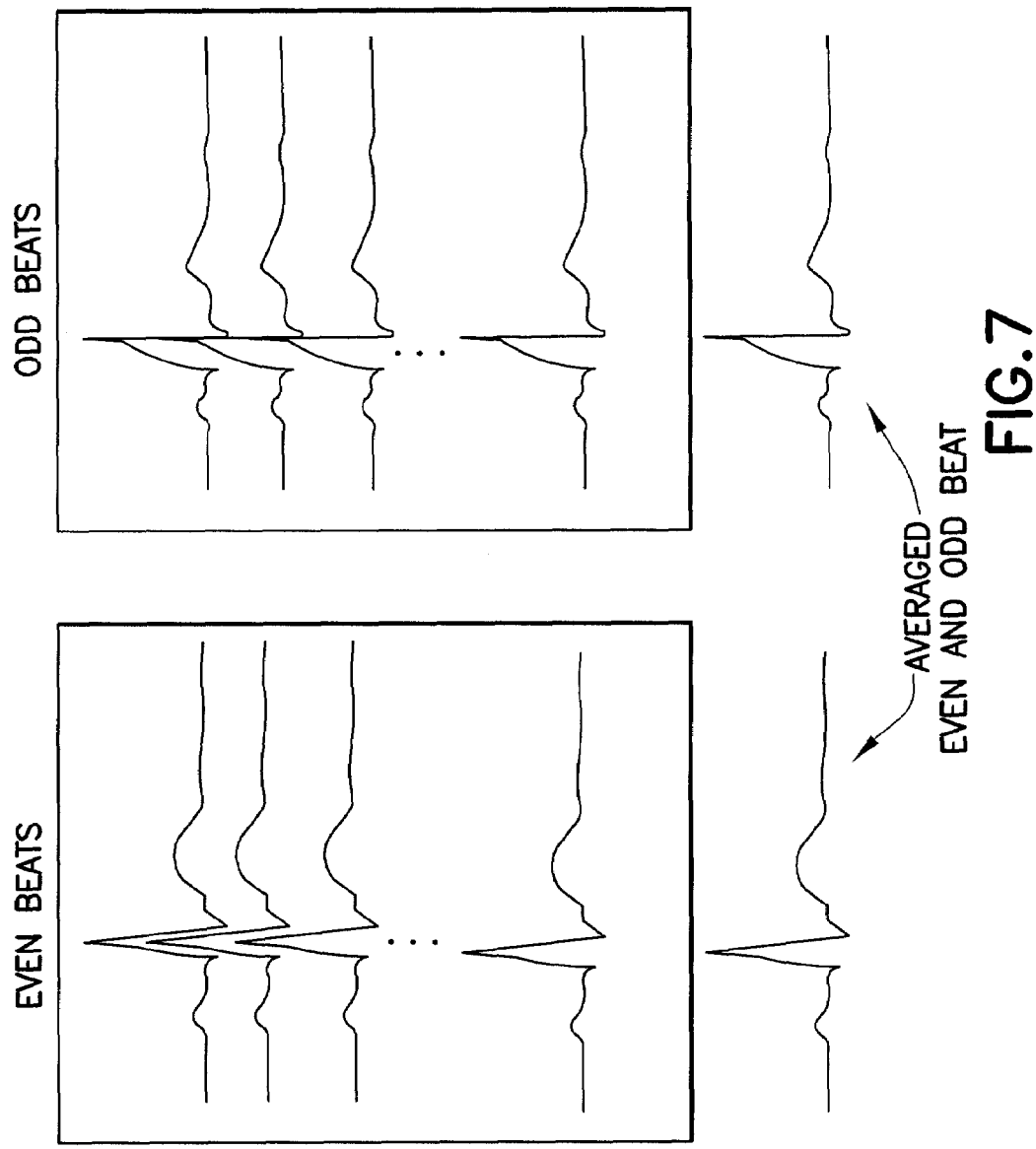

METHOD AND APPARATUS FOR ALGORITHM FUSION OF HIGH-RESOLUTION ELECTROCARDIOGRAMS

BACKGROUND OF INVENTION

This invention relates to the analysis of electrocardiograms (ECGs). More specifically, the invention relates to methods and apparatus for analyzing ECGs.

In hospitals or other health-care settings, it is frequently necessary to observe critical physiological conditions of a patient, including cardiovascular conditions. Such cardiovascular condition data includes ECGs acquired using electrodes applied to the patient.

A typical ECG management system comprises a database of ECGs plus applications software. The ECG management system receives ECG data from a multiplicity of instruments via a plurality of networks, analyzes that ECG data using various programs such as a serial comparison program, generates reports containing the results of the analysis, and then routes those reports to various systems and peripheral devices.

The accuracy of any ECG analysis expert software tool is directly dependent upon the quality of the signal it acquires. In 1979, Marquette Medical Systems introduced an electrocardiograph that simultaneously acquired all of the leads from the 12-lead electrocardiogram. Prior to this time, all commercially available electrocardiographs could only acquire 3 leads at a time. Simultaneous recording was adopted so that the computer could use all signals from all 12 leads to properly detect and classify each QRS complex. The program also applied digital filters which removed power line noise and baseline sway. Typically, ECG data is acquired from the 12 leads for a period of 10 seconds.

All ECG analysis computer programs are composed of two parts: one which measures the waveforms, the other which does the interpretation based on these measurements. The main task of the measurement section is to find the location of the major reference points (that is, the onsets and offsets of the P, QRS and T complexes). After the onsets and offsets of the P, QRS, and T complexes have been demarcated, the waves within each complex are measured according to published standards. These amplitudes and durations result in a measurement matrix containing more than 1000 values. This is then passed to the criteria portion of the ECG analysis program so that it can generate an interpretation, including diagnostic statements referenced via a statement library.

Recent progress in noninvasive electrocardiology has introduced more interesting features for use in diagnosis, including T wave alternans (TWA), QT dispersion (QTD), QT dynamicity (QTDN), short-time heart rate variability (HRV), etc.

T Wave Alternans Alternans is a subtle beat-to-beat change in the repeating pattern of an ECG that can be indicative of electrical instability of the heart and increased susceptibility to sudden cardiac death. Alternans results in an ABABAB . . . pattern of variation of the waveform shape between successive beats in an ECG waveform, and the level of cardiac stability is taken as a characterization of an individual's cardiac electrical stability. In humans, it has been found that the T wave is the best interval of the ECG complex for detecting alternans. That is, a level of variation in the T waves of alternating beats is the best indicator of a patient's level of alternans.

QT Dispersion The calculation of QT interval dispersion from the standard 12-lead ECG is a promising noninvasive measurement of inhomogeneity in myocardial repolarization. The QT dispersion measurement is useful for different clinical applications, namely for assessment of patients at risk for lethal ventricular arrhythmias and for differentiating patients with acute myocardial infarction (AMI) from those with noncardiac chest pain. To compute QT dispersion, one needs to measure QRS complex onset and T wave offset to calculate the QT interval for each lead. A computerized automatic method for calculating QT dispersion was presented by Xue and Reddy in "Algorithms for Computerized QT Analysis", Journal of Electrocardiology, Vol. 30 Supplement, pp. 198–203 (1998).

QT DynamicityIt is known that prolongation of the QT interval may be a marker for sudden death. QT dynamicity is used to examine the beat-to-beat change of the QT interval due to changes in heart rate or T morphology.

Heart Rate Variability The autonomic nervous system is the part of the vertebrate nervous system that regulates involuntary action, such as the heart. A significant relationship exists between the autonomic nervous system and cardiovascular mortality, including sudden cardiac death (SCD). Heart rate variability (HRV) is a recognized quantitative marker of autonomic activity. Many commercial devices provide automated measurement of HRV. The term "heart rate variability" has become the conventionally accepted term to describe variations of both instantaneous heart rate and RR intervals (i.e., the interval between consecutive heart beats). Standards for the measurement of HRV are set forth in "Heart Rate Variability: Standards of Measurement, Physiological Interpretation, and Clinical Use", by the Task Force of the European Society of Cardiology and the North American Society of Pacing and Electrophysiology, Circulation, Vol. 93, No. 5, Mar. 1, 1996, pp. 1043–1065.

Late Potentials Late potential is the small amplitude signal detected at the end of the QRS complex, so-called "late" potential. Since late potential has very low amplitude (usually lower than 50 μV), it is detected by using high-resolution ECG through a signal averaging technique. In this case "high resolution" means higher amplifier gain (around 1 μV/LSB vs. 5 μV/LSB (least significant bit)) and higher sampling frequency (1000 samples per second or more vs. 125–500 samples per second for conventional ECG). It has been proposed to combine T-wave alternans and late potentials for identifying high-risk patients with impaired left ventricular function. See Kondo et al., "Clinical usefulness of the combination of T wave alternans and late potentials for identifying high-risk patients with moderately or severely impaired left ventricular functions", Circulation, Vol. 65, No. 7, pp. 649–553 (2001). The late potentials were determined on signal-averaged ECGs.

Intra-QRS Analysis Intra-QRS analysis examines small notches inside the QRS complex based on signal-averaged high-resolution ECGs. It has been shown that the significant notches found inside the QRS complex are correlated with ischemic events before and after PTCA. See Endt et al., "Identification of post-myocardial infarction patients with ventricular tachycardia by time-domain intra-QRS analysis of signal-averaged electrocardiogram and magnetocardiogram", Med. Biol. Eng. Comput., Vol. 38, No. 6, pp. 659–665 (2000) Many other expert software tools are being used in cardiology. For example, high-resolution ECGs, also referred to as signal-averaged ECGs (SAECGs), have been widely used in cardiology clinical practice. Late potentials detection of SAECGs has been proven useful for predicting lethal ventricular tachyarrhythmia and ventricular fibrillation (VT/VF), and P-wave SAECGs have been used for predicting atrial fibrillation (AF). During the process of high-resolution detection, 200–400 heart beats signals are acquired with higher sampling frequency (1000 Hz vs. 500 Hz for standard 12-lead ECG), and higher resolution (about 1 μV least significant bit vs. 5 μV for standard 12-lead ECG). In current cardiographs, the end results of high-resolution detection are averaged ECGs from three orthogonal leads: X, Y, Z, and some measurements like P wave and QRS duration from the averaged leads. In practice, also 12-lead electrodes are put on a patient's body surface.

With the 200–400 heart beats (5 to 10 minutes) of high-resolution signals from X, Y, Z leads plus standard 12-lead ECGs, a cardiologist has much more information than the data acquired by regular 10-sec 12-lead ECGs. There is a need for methods of extracting more useful features from this increased volume of acquired data for more accurate and more efficient diagnosis of abnormal activity of the heart.

SUMMARY OF INVENTION

The present invention is directed to methods and apparatus for multiple algorithm fusion of high-resolution ECG data. The disclosed embodiments use signals collected during high-resolution processing to not only detect new features such as late potential, T wave alternans (TWA), QT dispersion (QTD), QT dynamicity (QTDN), short-time heart rate variability (HRV), and intra QRS, but also to improve the quality of those features. For example, the reproducibility of QT dispersion measurements can be improved with many more heart beats of data. More importantly, the combined features (feature fusion) from this group can improve the accuracy of the diagnosis in clinically relevant groups. For example, results from late potentials, T wave alternans and QT dynamicity analyses can be fused to predict ventricular tachyarrhythmia after myocardial infarction and atrial fibrillation; results from QT dispersion and intra-QRS analyses can be fused for ischemia detection and prediction; and results from HRV, QT dispersion and QT dynamicity can be fused for predicting sudden cardiac death after myocardial infarction.

One aspect of the invention is a method for noninvasive ECG detection and diagnosis, comprising the following steps: acquiring high-resolution ECG data from a patient; processing the acquired data in accordance with two or more different ECG analysis algorithms; and deriving a prediction score for a particular clinical end point as a function of the respective results of those ECG analysis algorithms.

Another aspect of the invention is a system for noninvasive ECG detection and diagnosis, comprising: a multiplicity of electrodes applied to a patient, a data acquisition system for acquiring high-resolution ECG data from the patient; and a processor programmed to process the acquired data in accordance with two or more different ECG analysis algorithms, and then derive a prediction score for a particular clinical end point as a function of the respective results of those ECG analysis algorithms.

A further aspect of the invention is a method for noninvasive ECG detection and diagnosis, comprising the following steps: (a) acquiring high-resolution ECG data from a patient using the X, Y and Z leads of a Frank lead system; (b) dividing the high-resolution ECG data into even beat and odd beat groups; (c) averaging beats in said even and odd beat groups separately; (d) determining the variance of T wave morphology of all even beats for each of said X, Y, Z leads; (e) determining the variance of T wave morphology of all odd beats for each of said X, Y, Z leads; (f) determining the variance of T wave morphology between even and odd averaged beats for each of the X, Y, Z leads; and (g) determining T wave alternans as a function of the results of steps (d)–(f) by analysis of variance.

Yet another aspect of the invention is a system for noninvasive ECG detection and diagnosis, comprising: a multiplicity of electrodes applied to a patient, a data acquisition system for acquiring high-resolution ECG data from the patient using the X, Y and Z leads of a Frank lead system; and a processor programmed to process the acquired data in accordance with a T wave alternans algorithm comprising the following steps: (a) dividing the high-resolution ECG data into even beat and odd beat groups; (b) averaging beats in said even and odd beat groups separately; (c) determining the variance of T wave morphology of all even beats for each of said X, Y, Z leads; (d) determining the variance of T wave morphology of all odd beats for each of said X, Y, Z leads; (e) determining the variance of T wave morphology between even and odd averaged beats for each of the X, Y, Z leads; and (f) determining T wave alternans as a function of the results of steps (c)–(e) by analysis of variance.

Other aspects of the invention are disclosed and claimed below.

BRIEF DESCRIPTION OF DRAWINGS

FIG. 7 is a diagram showing the application of a T wave alternans algorithm to high-resolution ECG in accordance a further aspect of the invention.

Reference will now be made to the drawings in which similar elements in different drawings bear the same reference numerals.

DETAILED DESCRIPTION

Figure 1:
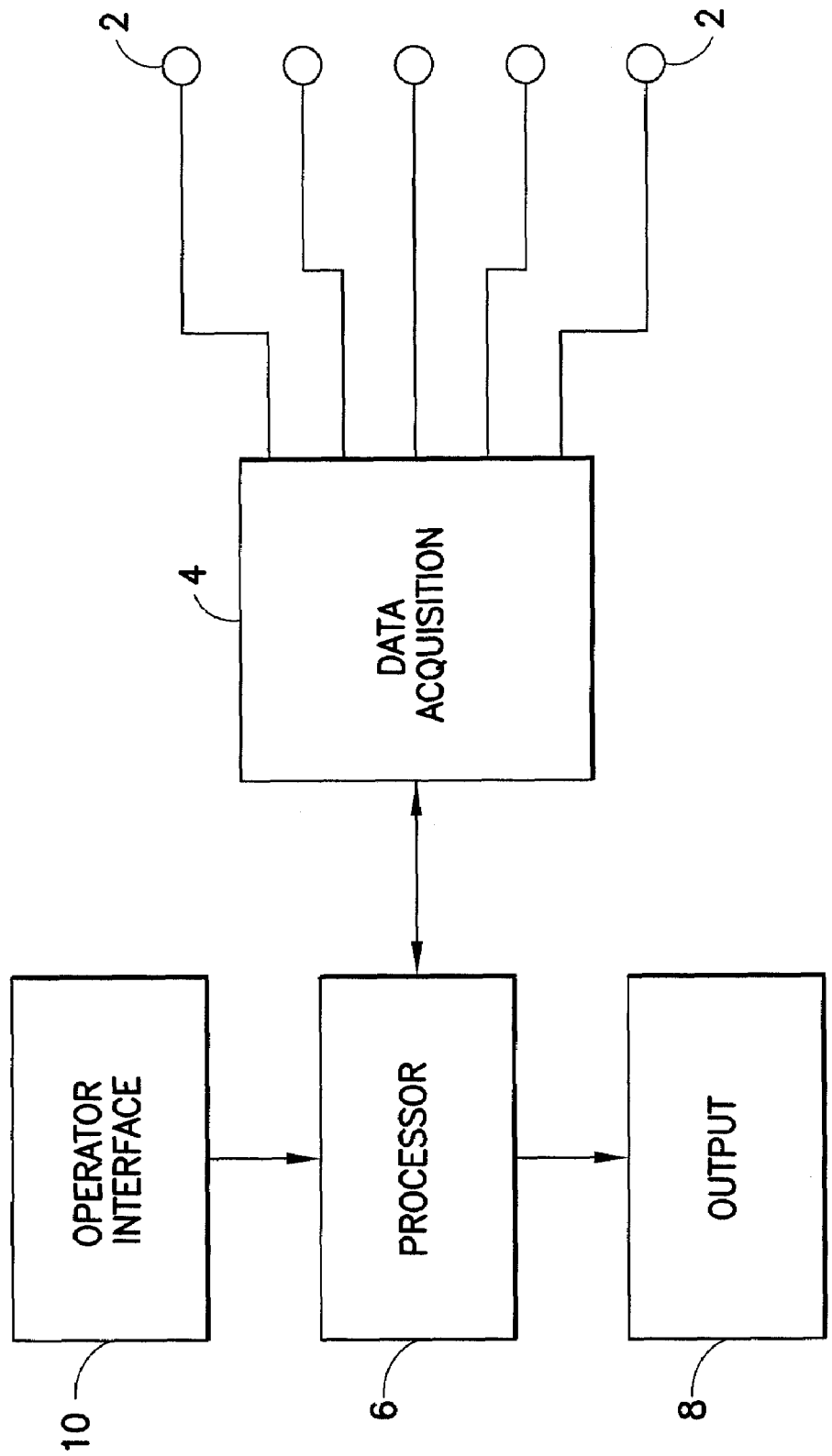
FIG. 1 is a block diagram showing a system in accordance with one embodiment of the invention.

Referring to FIG. 1, an electrocardiogram (ECG) system in accordance with one embodiment of the present invention comprises a set of electrodes 2 that are attached to the patient's body, a data acquisition system 4 that receives and stores ECG waveform data output from the various electrodes 2, and a data processor 6 for processing the acquired ECG waveform data in accordance with ECG analysis and algorithm fusion applications software. The data acquisition system 4 acquires samples of signals produced by both orthogonal X, Y, Z leads and the standard 12-lead system. A system operator can select the operating mode of the processor via inputs to an operator interface 10. The results of the ECG analyses and subsequent algorithm fusion are sent from the processor to one or more output devices 8, which may include a display monitor, a printer, a storage medium, etc.

Figure 2:
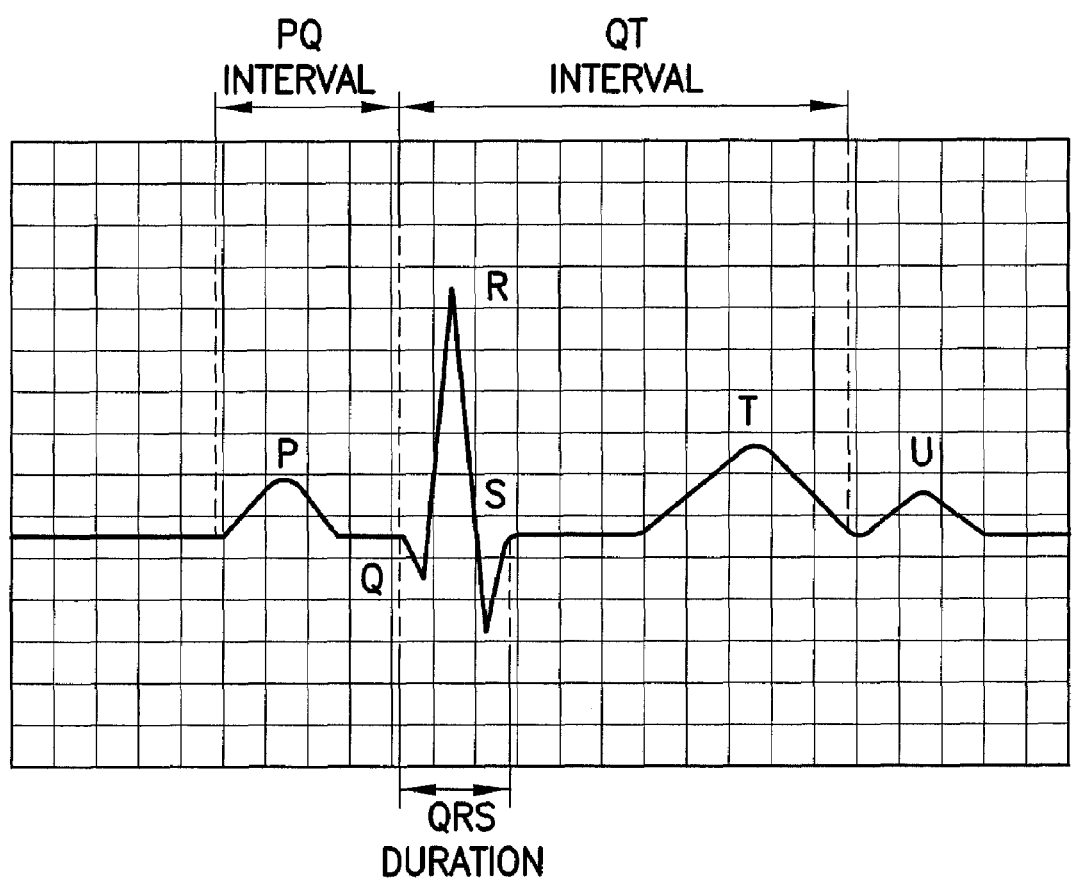
FIG. 2 is a graph showing conventional ECG nomenclature.

The electrodes 2 are attached to a patient's skin and positioned to detect electrical signals produced by the patient's heart. The electrodes include an electrically conductive gel that contacts the patient's skin and conducts to the electrode any electrical signals that are present at the skin. The patient's heart produces an electrical signal that is referred to as an ECG waveform. The shape of a typical ECG waveform is shown in FIG. 2. The standard nomenclature identifies a P wave, a QRS complex, a T wave, and a U wave. The interval from the onset of the QRS complex to the end of the T wave is referred to as the QT interval.

An ECG waveform for a single beat is typically referred to as a PQRST complex. The P wave appears at initiation of the beat and corresponds to activity in the atria, while the QRST complex follows the P wave and corresponds to ventricular activity. The QRS component represents the electrical activation of the ventricles, while the T wave represents the electrical recovery thereof. The ST segment is a relatively quiescent period. In humans, it has been found that the T wave is the best interval of the ECG complex for detecting alternans. That is, a level of variations in the T waves of alternating beats is a good indicator of a patient's cardiac electrical stability.

The ECG signal produced by the patient's heart decreases as a function of the distance from the heart at which it is measured. Accordingly, an ECG signal detected by an electrode 2 will vary from the actual ECG signal based on the placement of the electrode relative to the heart. An accurate approximation of the actual ECG signal may be generated by combining signals from multiple electrodes having known placement relative to the heart.

The ECG signal measured at the body surface may be represented by modeling the heart as a three-dimensional dipole source that produces an electrical signal that varies based on the distance from the heart in the X, Y and Z directions. Use of the dipole vector model of the heart has lead to the development of clinical systems that measure the X, Y and Z components of the dipole source through a linear combination of several electrodes. One known XYZ system is the Frank lead system.

Figure 4:
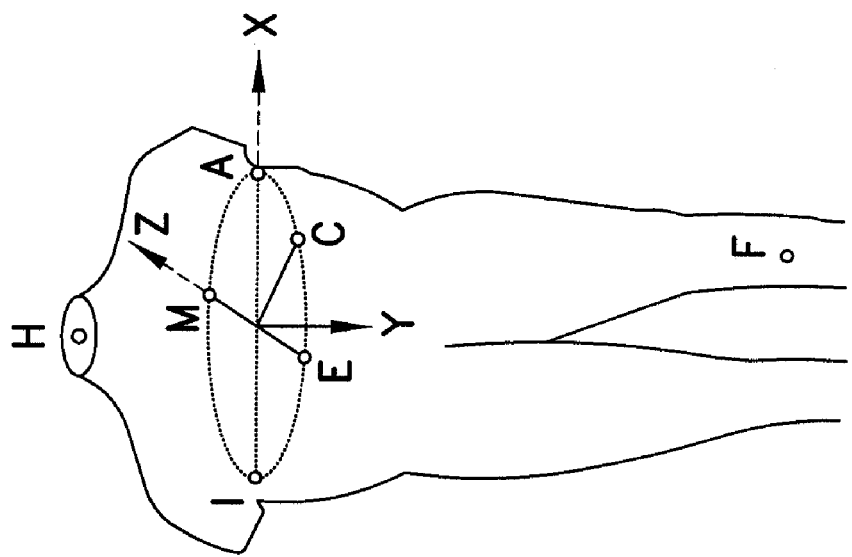
FIG. 4 is a drawing showing the Frank lead electrode system.
Figure 3:
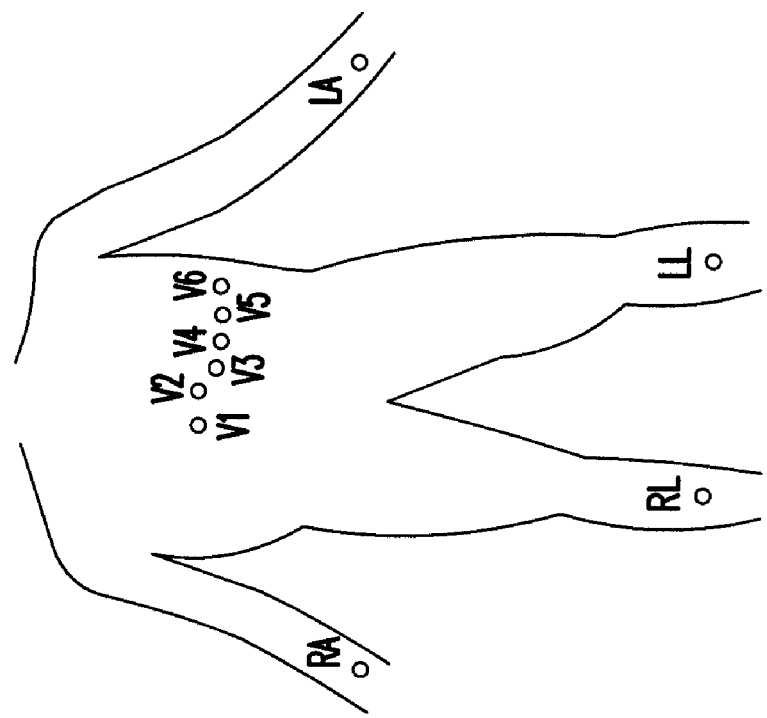
FIG. 3 is a drawing showing the standard 12-lead electrode system.

In accordance with one aspect of the present invention, ECG signals are sampled from both a standard 12-lead system as shown in FIG. 3 and an orthogonal X, Y, Z lead system as shown in FIG. 4. In the Frank lead system depicted in FIG. 4, seven electrodes, designated as H, F, I, E, C, A, M are applied to the body at the following locations: H, forehead or neck; F, left leg; I, E, C, A, M are located along the same transverse level: the fourth intercostal space if the patient is supine, or the fifth intercostal space if the patient is sitting; I, anterior axillary line; E, center of sternum; A, left anterior axillary line; C, at a 45 degree. angle between E and A; and M, center of spine. Since one can use lead v6 in FIG. 3 for lead A of FIG. 4, and lead v4 in FIG. 3 for lead C of FIG. 4, there are total 14 electrodes needed for the data collection.

Figure 5:
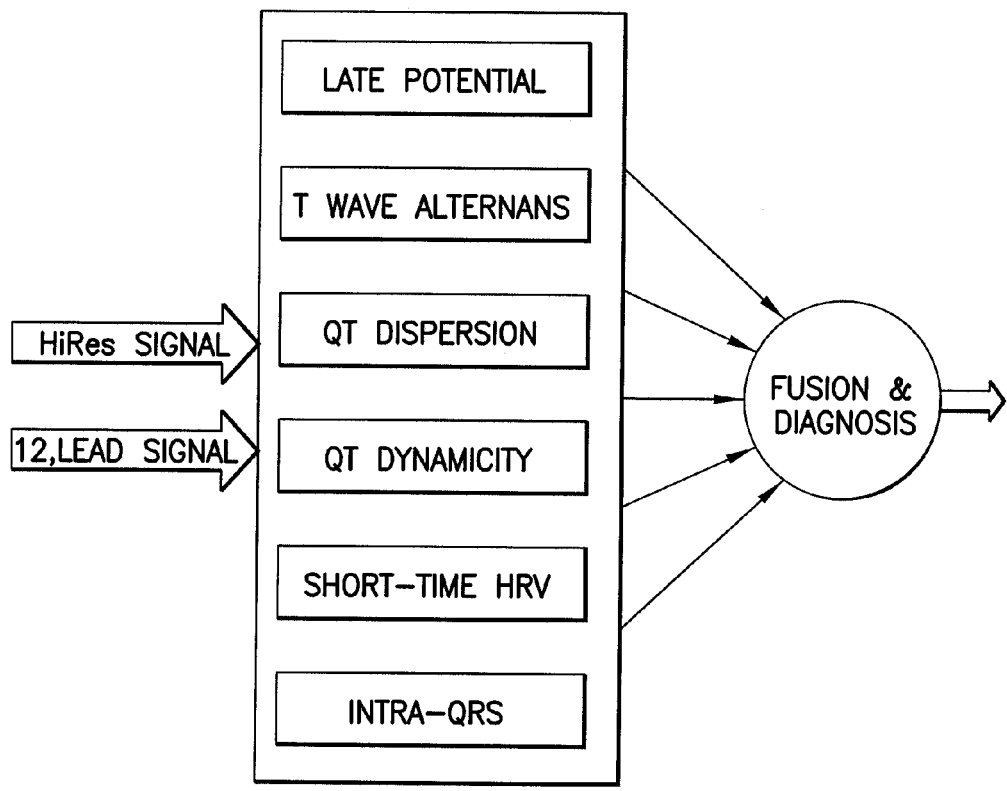
FIG. 5 is a flowchart of algorithm fusion for high-resolution ECG analysis in accordance with one aspect of the invention.

The acquired ECG data (i.e., high-resolution signals from the X, Y Z leads and 12-lead signals) are processed in each of a plurality of algorithm modules while data is being sampled, as shown in FIG. 5. It is necessary to use high-resolution ECG to obtain late potential. Current high-resolution ECG analysis already acquires 5–10 minutes of signal, but has not fused the outputs of separate algorithm modules as taught herein.

In accordance with one embodiment of the invention, six different algorithm modules process respective features In the ECG waveform data: late potential, T wave alternans, QT dispersion/complexity, QT dynamicity, short-time HRV, and intra-QRS notch detection. Each of the six algorithm modules are available on one and the same platform. The results of any two or more algorithm modules can be fused in combinations that depend on the particular clinically relevant group. Diagnosis is based on the results of algorithm fusion.

Figure 6:
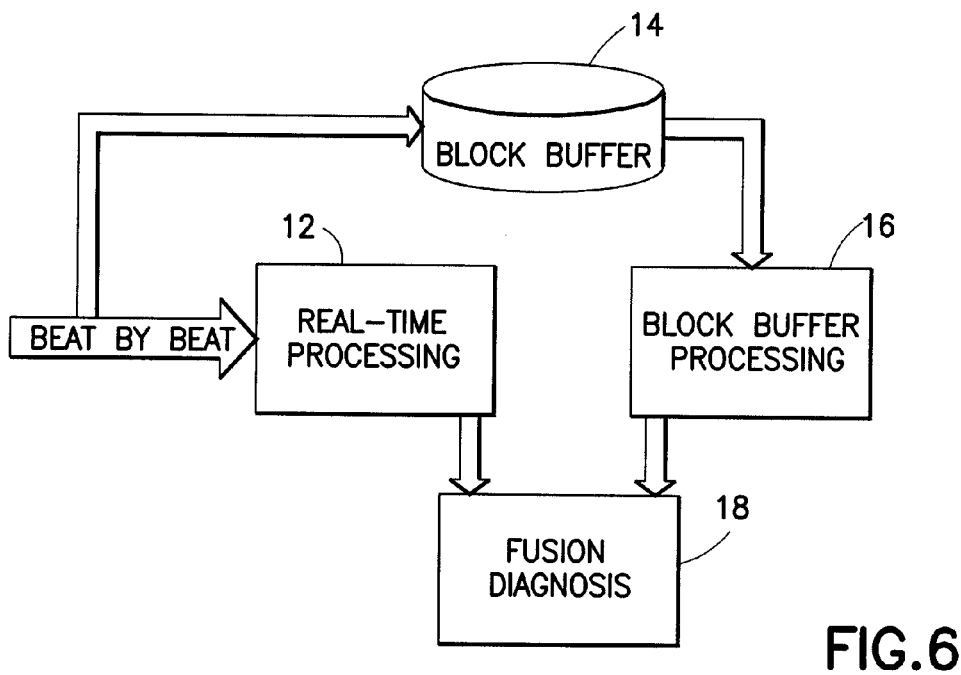
FIG. 6 is a flowchart showing three-stage processing performed during high-resolution ECG analysis in accordance with another aspect of the invention.

The fusion process in accordance with one aspect of the invention can be divided into three stages: real-time processing, buffer block processing, and fusion diagnosis, as shown in FIG. 6. Each of these stages can, for example, be executed by the processor 6 in FIG. 1. The task of the real-time processing (step 12 in FIG. 6) is to handle beat-by-beat processing needed for all algorithms, which includes beat alignment detection for averaging, ectopic beat detection for exclusion, on-line signal averaging for displaying and on-line parameter calculation for noise level monitoring. All of the data, including X, Y, Z Frank lead and standard 12-lead ECGs will be stored in a temporary buffer 14. The data sampling stops in the following situations: (a) the noise level of the averaged beat reaches a criteria level, e.g., 0.3 µV; (b) a maximum or target number of ECG cycles or heart beats to be averaged (set by the user) is reached; or (c) the user interrupts the process. The algorithm modules will perform their respective processes by using the data in the buffer (step 16 in FIG. 6). The final diagnosis is based on the fused results from all algorithm modules (step 18 in FIG. 6).

In accordance with various aspects of the invention, the results of high-resolution ECG waveform data processing by two or more algorithm modules can be fused in aid of diagnosis. The algorithms can be selected from the group of six algorithms described in more detail below. However, the broad concept of algorithmic fusion based on high-resolution (i.e., signal averaged) ECG data encompasses and anticipates the use of other algorithms in addition to those described below.

Late Potential The QRS late potential module and P wave high-resolution module have been implemented in existing cardiographs. Substantially the same algorithms, with minor modifications, can be a component of the fusion diagnostic process disclosed herein.

T Wave Alternans The T wave alternans algorithm is based on all three leads of the high-resolution ECG data acquisition. As shown in FIG. 7, the first step is to divide the high-resolution data into even beat and odd beat groups. The beats in the two groups are then averaged separately. T wave alternans are examined based on three pairs X, Y, Z. The algorithm compares intra-variance (i.e., within group variance) with extra-variance (i.e., between group variance) using a classic statistical analysis procedure called ANOVA analysis of variance. In this technique the presence of an effect is determined when the variance between groups is statistically larger than the variance within groups. The intra-variance is the variance of T wave morphology of all even beats, or all odd beats for the same lead; the extra-variance is the variance of T wave morphology between even and odd averaged beats. If the extra-variance for two of the three leads are significantly larger than the intra-variance for those leads, T wave alternans is positive; otherwise it will be negative.

QT Dispersion The known QT dispersion algorithm of Xue and Reddy (cited above) is based on 10-sec 12-lead ECGs. In accordance with one aspect of the present invention, QT dispersion is computed for multiple segments of 10-sec 12-lead ECGs. The final value of QT dispersion will be either average or median values of the QT dispersions of all segments. [Since regular QT dispersion is calculated from 10-second ECG segments, when 5–10 minutes of ECGs are available, we can take either the mean or median value of the multiplicity of 10-second-segment QT dispersion values to generate this final value of QT dispersion.] This method provides enhanced reproducibility of QT dispersion.

QT Dynamicity The QT dynamicity algorithm involves examining the beat-by-beat change of the QT interval due to changes in heart rate or T morphology. With 200–400 beats of ECG waveform data from the X, Y, Z leads, the processor can compute the short-time QT dynamicity with statistically meaningful confidence.

Short-Time HRV The heart rate variability algorithm measures HRV based on 5 or more minutes of heart beats, and is capable of measuring accurately the HF (4-sec rhythm) and the LF (10-sec rhythm) components of HRV. An estimate of the VLF (all rhythms shorter than 5 minutes) component is possible but less accurate. Knowing just the HF and LF components is sufficient to give useful information about the risk of SCD after myocardial infarction, diabetic neuropathy or graft rejection after cardiac transplantation among others, as reported by Malik, cited above.

Intra-QRS Analysis The intra-QRS algorithm examines small notches inside the QRS complex based on signal-averaged high-resolution ECGs. As discussed above, Endt has reported that the significant notches found inside the QRS complex are correlated with ischemic events before and after PTCA. One aspect of the present invention will match the notches inside the QRS complex from averaged X, Y, Z beats.

Fusion Diagnosis The results of the applying the foregoing algorithms to the high-resolution ECG data are then fused and used for the purpose of diagnosis. Algorithm fusion can be performed in clinically relevant groups. For example, the results from the late potential (either QRS or P wave), T wave alternans and QT dynamicity algorithm modules can be fused for VT prediction and atrial fibrillation. In addition, the results from the QT dispersion and intra-QRS algorithm modules can be fused for the purpose of ischemia detection and prediction. Also the results of the Late potential of QRS, HRV, QT dispersion and QT dynamicity algorithm modules can be fused for predicting sudden cardiac death for post-myocardial infarction patients.

An algorithm fusion model takes the outputs from different algorithms as its input parameters. This model's output is the prediction score (ranging from 0 to 100, with 0 meaning least likely and 100 meaning most likely) for particular clinical end points, which can be, for example, sudden cardiac death or sustained ventricular tachycardia. The predictive model is trained with clinically confirmed data for both input and output. The training methods include both neural network (nonlinear regression) or linear regression. After the model has been trained with known outcome output, it can generate the predictive score for unknown outcome patients. This fusion model can generate better predictive accuracy (with both good sensitivity and specificity) than use of a single algorithm output without fusion.

The advantages of algorithm fusion as disclosed herein are manifold. Multiple noninvasive features can be generated from the same amount of data collected for high-resolution ECGs. The technique provides improved accuracy and efficiency of the noninvasive ECG detection and diagnosis processes. Also, algorithm fusion of high-resolution ECG data reduces patient/technician study time.

While the invention has been described with reference to preferred embodiments, it will be understood by those skilled in the art that various changes may be made and equivalents may be substituted for members thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The invention claimed is:

1. A method for noninvasive ECG detection and diagnosis, comprising the following steps:
    acquiring high-resolution ECG data from a patient, the resolution being equal to or better than about 1 microvolt for the least significant bit of said ECG data;
    processing said acquired data in accordance with two or more different ECG analysis algorithms in respective software modules of a data processor;
    processing the outputs of said respective software modules in said data processor to derive a prediction score for a particular clinical end point as a function of the respective results of said two or more ECG analysis algorithms; and
    outputting signals representing said prediction score from said data processor to an output device.

2. The method as recited in claim 1, further comprising the step of training a predictive model with clinically confirmed data for both input and output, wherein said predictive model is used for said prediction score derivation.

3. The method as recited in claim 1, wherein said particular clinical end point is sudden cardiac death.

4. The method as recited in claim 1, wherein said particular clinical end point is sustained ventricular tachycardia.

5. The method as recited in claim 1, wherein said particular clinical end point is ischemia.

6. The method as recited in claim 1, wherein said ECG analysis algorithms comprise late potential, T wave alternans and QT dynamicity algorithms.

7. The method as recited in claim 1, wherein said ECG analysis algorithms comprise QT dispersion and intra-QRS algorithms.

8. The method as recited in claim 1, wherein said ECG analysis algorithms comprise heart rate variability, QT dispersion and QT dynamicity algorithms.

9. The method as recited in claim 1, wherein said data acquisition step uses the X, Y and Z leads of a Frank lead system.

10. The method as recited in claim 9, wherein one of said ECG analysis algorithms is a T wave alternans algorithm comprising the following steps:
    dividing the high-resolution ECG data into even beat and odd beat groups;
    averaging beats in said even and odd beat groups separately;
    determining the variance of T wave morphology of all even beats for each of said X, Y, Z leads;
    determining the variance of T wave morphology of all odd beats for each of said X, Y, Z leads; and
    determining the variance of T wave morphology between even and odd averaged beats for each of said X, Y, Z leads.

11. The method as recited in claim 9, wherein said data acquisition step also uses leads of a standard 12-lead system.

12. The method as recited in claim 11, wherein one of said ECG analysis algorithms is a QT dispersion algorithm comprising the following steps:

computing a respective QT dispersion value for each of a multiplicity of successive segments of 12-lead ECGs; and computing a mean or median value of said QT dispersion values.

13. A system for noninvasive ECG detection and diagnosis, comprising: a multiplicity of electrodes applied to a patient, a data acquisition system for acquiring high-resolution ECG data from the patient, the resolution being equal to or better than about 1 microvolt for the least significant bit of said ECG data; and a processor programmed to process said acquired data in accordance with two or more different ECG analysis algorithms, and derive a prediction score for a particular clinical end point as a function of the respective results of said two or more ECG analysis algorithms.

14. The system as recited in claim 13, wherein said processor is programmed to use a predictive model for said prediction score derivation, said predictive model being trained with clinically confirmed data for both input and output.

15. The system as recited in claim 13, wherein said particular clinical end point is sudden cardiac death.

16. The system as recited in claim 13, wherein said particular clinical end point is sustained ventricular tachycardia.

17. The system as recited in claim 13, wherein said particular clinical end point is ischemia.

18. The system as recited in claim 13, wherein said ECG analysis algorithms comprise late potential, T wave alternans and QT dynamicity algorithms.

19. The system as recited in claim 13, wherein said ECG analysis algorithms comprise QT dispersion and intra-QRS algorithms.

20. The system as recited in claim 13, wherein said ECG analysis algorithms comprise heart rate variability, QT dispersion and QT dynamicity algorithms.

21. The system as recited in claim 13, wherein said data acquisition system comprises the X, Y and Z leads of a Frank lead system.

22. The system as recited in claim 21, wherein one of said ECG analysis algorithms executed by said processor is a T wave alternans algorithm comprising the following steps:
    dividing the high-resolution ECG data into even beat and odd beat groups;
    averaging beats in said even and odd beat groups separately;
    determining the variance of T wave morphology of all even beats for each of said X, Y, Z leads;
    determining the variance of T wave morphology of all odd beats for each of said X, Y, Z leads; and
    determining the variance of T wave morphology between even and odd averaged beats for each of said X, Y, Z leads.

23. The system as recited in claim 21, wherein said data acquisition system further comprises leads of a standard 12-lead system applied to the patient.

24. The system as recited in claim 23, wherein one of said ECG analysis algorithms executed by said processor is a QT dispersion algorithm comprising the following steps:
    computing a respective QT dispersion value for each of a multiplicity of successive segments of 12-lead ECGs; and
    computing a mean or median value of said QT dispersion values.

25. A method for noninvasive ECG detection and diagnosis, comprising the following steps:
    (a) acquiring high-resolution ECG data from a patient using the X, Y and Z leads of a Frank lead system, the resolution being equal to or better than about 1 microvolt for the least significant bit of said ECG data;
    (b) dividing the high-resolution ECG data into even beat and odd beat groups;
    (c) averaging beats in said even and odd beat groups separately;
    (d) determining the variance of T wave morphology of all even beats for each of said X, Y, Z leads;
    (e) determining the variance of T wave morphology of all odd beats for each of said X, Y, Z leads;
    (f) determining the variance of T wave morphology between even and odd averaged beats for each of said X, Y, Z leads; and
    (g) determining T wave alternans as a function of the results of steps (d)–(f) by analysis of variance.

26. A system for noninvasive ECG detection and diagnosis, comprising: a multiplicity of electrodes applied to a patient, a data acquisition system for acquiring high-resolution ECG data from the patient using the X, Y and Z leads of a Frank lead system, the resolution being equal to or better than about 1 microvolt for the least significant bit of said ECG data; and a processor programmed to process said acquired data in accordance with a T wave alternans algorithm comprising the following steps:
    (a) dividing the high-resolution ECG data into even beat and odd beat groups;
    (b) averaging beats in said even and odd beat groups separately;
    (c) determining the variance of T wave morphology of all even beats for each of said X, Y, Z leads;
    (d) determining the variance of T wave morphology of all odd beats for each of said X, Y, Z leads;
    (e) determining the variance of T wave morphology between even and odd averaged beats for each of said X, Y, Z leads; and
    (f) determining T wave alternans as a function of the results of steps (c)–(e) by analysis of variance.

* * * * *